United States Patent [19]

Boerma

[11] 3,959,181

[45] May 25, 1976

[54] CATALYSTS

[75] Inventor: Hiepke Boerma, Vlaardingen, Netherlands

[73] Assignee: N.V. Internationale Octrooi Maatschappij "Octropa", Rotterdam, Netherlands

[22] Filed: Dec. 12, 1972

[21] Appl. No.: 314,396

[30] Foreign Application Priority Data

Dec. 17, 1971 Netherlands.................... 7158625

[52] U.S. Cl. .............................................. 252/459
[51] Int. Cl.$^2$...................... B01J 29/10; B01J 29/20
[58] Field of Search................................... 252/459

[56] References Cited
OTHER PUBLICATIONS
"Neues aus der Technik", 1, pp. 2–3, 3/71.

Primary Examiner—Paul F. Shaver
Attorney, Agent, or Firm—Kaufman & Kramer

[57] ABSTRACT

A process for preparing a supported nickel catalyst is described in which precipitation of the nickel on a support occurs by mixing an aqueous solution of a nickel salt, a solution of an alkali metal carbonate and an alkali metal hydroxide containing, by weight of the hydroxide, at least 10% of the carbonate and a support to form a suspension which during the whole of the precipitation is between 75° and 100°C, is at a pH between 8.0 and 10 and has an alkalinity greater than 0.010N.

4 Claims, No Drawings

CATALYSTS

The invention relates to the preparation of a nickel-based catalyst. nickel-based catalysts are very widely used, particularly as hydrogenation catalysts. Such catalysts are often supported catalysts.

It has been proposed to precipitate nickel hydroxide from an aqueous solution of a nickel salt using aqueous alkali metal carbonate. A support material can be present during the precipitation or can be added later. Materials that can be used as supports include aluminas and silicas (e.g. silica-containing materials), such as kieselguhrs. A preferred such process is claimed in our UK 60499/70, corresponding to Netherlands 7117619. (Note this is not a prior publication.)

It has now been found that an excellent nickel-based catalyst is obtained if precipitation occurs by mixing
 a. an aqueous solution of alkali metal carbonate and alkali metal hydroxide, containing, by weight of alkali metal hydroxide, at least 10% of alkali metal carbonate;
 b. an aqueous solution of a nickel salt; and
 c. a support material, preferably a silica, to form a suspension that is in the temperature range 75° to 100°C, preferably 85° to 95°C, and has a pH of 8.0 to 10.0, preferably 8.5 to 9.5, and the suspension is then separated, preferably by filtration, after precipitation of the nickel is complete. After separation the suspension is preferably washed. The alkali metal is preferably sodium.

The support material can be added (a) directly, (b) in suspension in water, (c), preferably, in suspension in the aqueous solution of the nickel salt or (d) in suspension in the mixture of alkali metal carbonate and alkali metal hydroxide solutions. When the support material is added in suspension in the solution of alkali metal carbonate and hydroxide, preferably care must be taken to ensure that the support material and the solution are not in contact for an undue time, preferably less than 5 minutes.

When the support material is a silica, the weight ratio of Ni to $SiO_2$ is preferably between 0.5 and 4, particularly preferably between 2 and 3.

Preferably the temperature is within a range of not more than 5°C during the precipitation, particularly preferably not more than 2°C. The temperature can be achieved in any convenient manner, for instance by heating the suspension with steam-coils, blowing in steam or by using heated reactants. The pH is particularly preferably kept within the range 9.0–9.5. The pH referred to throughout is the pH of filtrate cooled to 25°C.

Another important parameter is the excess of alkali present during precipitation, called the alkalinity. This alkalinity should preferably be maintained above 0.010N.

The alkalinity is determined in the filtrate after cooling to 25°C by titration with acid, using phenolphthalein as indicator. The rate of addition of the reactants, for instance the addition of nickel salt or the addition of the mixture of alkali metal carbonate and alkali metal hydroxide solutions, can be used to control the alkalinity. The alkalinity should preferably be kept constant. A continuous process is preferred.

The nickel salt used is preferably nickel sulphate. Nickel nitrate, acetate, chloride and formate are examples of other suitable nickel salts. The normality of the salt solution is preferably between 0.5 and 3.0, particularly preferably between 1.5 and 2.0.

In a continuous process the suspension preferably has a mean residence time of less than 60, preferably between 4 and 20 and especially between 5 and 15 minutes, in a mixing vessel, where at least most of the precipitation occurs, and is then separated, preferably by filtration, to give the catalyst. The time after the suspension leaves the mixing vessel and before separation is preferably less than 15 minutes.

The suspension preferably should be at a temperature in the range of 75° to 90°C if it is filtered.

Preferred support materials are silicas, in particular silicas that are normally described as amorphous, i.e. silicas that contain, as estimated by X-ray diffraction, less than 50% of crystalline material. For such amorphous silicas the weight ratio of nickel to silica is preferably 2.0 or higher. When the crystalline content is higher, optimum catalysts can be prepared with lower weight ratios of nickel to silica, for instance from a weight ratio of 0.5.

A related property for which the above preferences apply is alkaline solubility. Thus for silicas with high, above 70%, alkaline solubility the weight ratio of nickel to silica is preferably above 2. For silicas with lower alkaline solubility lower weight ratios of nickel to silica are preferred, for instance from a weight ratio of 0.5.

Alkaline solubility is measured, for example, by stirring the silica at about 90°C in 1N sodium hydroxide solution and measuring the percentage dissolved after 10 minutes compared with sodium metasilicate taken as 100%.

As explained after precipitation and separation the catalyst is usually converted to an active form by, for example, drying and then activation using hydrogen and then, in appropriate cases, passivation using $N_2$ air. Such process steps are very well-known. It is to be understood that in this specification, when the context permits, the term catalyst includes both unactivated catalyst and activated catalyst.

Catalysts obtained by processes according to the invention are useful particularly as hydrogenation catalysts, for instance in the hydrogenation of aromatic compounds, such as benzene and phenol; methanation; fat hardening, including fatty acid hardening; reduction of nitrile and nitro compounds; reduction of aldehydes to alcohols; conversion of glucose to sorbitol; and reduction of sulpholene to sulpholane.

In this specification all percentages and figures are by weight unless otherwise indicated.

The invention will now be illustrated by the following Examples.

EXAMPLES 1 TO 6

Catalysts were prepared by a continuous process according to the invention at a temperature of 90°C, a pH of 9.5, using kieselguhr as support material, a Ni/$SiO_2$ ratio in the product of 2.5 and the following percentages, by volume, of 2N sodium carbonate in 1.7N sodium hydroxide 5 (Comp. 1), 10, 15, 20, 40, 60 and 80.

The catalysts made according to the invention had excellent properties. The comparison using 5% of sodium carbonate did not lead to a good catalyst.

EXAMPLES 7 TO 18

Catalysts were prepared by a continuous process according to the invention with a residence time of 8 minutes, 15%, by volume, 2N sodium carbonate in 1.7N sodium hydroxide, kieselguhr as support material and a Ni/SiO$_2$ ratio in the product of 2.5. The pHs and temperatures used are given in Table I.

TABLE I

| Temp. (°C) | pH | Quality of Catalyst | Temp. (°C) | pH | Quality of Catalyst |
|---|---|---|---|---|---|
| 80 | 8.5 | Good | 90 | 9.5 | Excellent |
| 80 | 9.0 | Good | 90 | 10.0 | Good |
| 80 | 9.5 | Excellent | 95 | 8.5 | Good |
| 80 | 10.5 | Good | 95 | 9.0 | Excellent |
| 90 | 8.5 | Good | 95 | 9.5 | Excellent |
| 90 | 9.0 | Excellent | 95 | 10.0 | Excellent |

EXAMPLES 19 TO 25

Table II gives the quality of catalysts obtained using silicas of varying alkaline solubility using a continuous process according to the invention with a residence time of 8 minutes, a temperature of 90°, 25%, by volume, 2N sodium carbonate in 1.7N sodium hydroxide and a Ni/SiO$_2$ ratio in the product of 2.5.

TABLE II

| Alkaline solubility | Quality of Catalyst |
|---|---|
| 68 | Excellent |
| 100 | Excellent |
| 22 | Good |
| 43 | Somewhat better |
| 50 | Excellent |
| 65 | Excellent |

EXAMPLES 26 AND 27

Table III gives the results obtained with catalysts prepared as described under Examples 1 to 6 except as stated in the hydrogenation of benzene using standard conditions, e.g. 70°C. The activity is defined as the number millimoles benzene converted per minute per gram of nickel.

TABLE III

| | % Na$_2$CO$_3$[1] | pH[2] | % Ni | Activity |
|---|---|---|---|---|
| Commercial Catalyst | — | — | 42.6 | 0.5 |
| Comparison | 5 | 9.5 | 44.6 | 0.15 |
| Example 26 | 10 | 9.5 | 42.9 | 0.81 |
| Example 27 | 25 | 9.25 | 43.2 | 0.75 |

[1]Volume % 2N sodium carbonate in 1.7N sodium hydroxide.
[2]During precipitation

What is claimed is:
1. An alkaline precipitation process for preparing a kieselguhr supported nickel catalyst in which an aqueous solution of a nickel salt, an aqueous solution of an alkali metal carbonate and an alkali metal hydroxide, said solution containing, by weight of the hydroxide, at least 10% of the carbonate, and kieselguhr are mixed to form a suspension that, throughout the precipitation,
 a. is within a 5°C. temperature range within the range of 75° to 100°C.,
 b. is at a pH of 8.0 to 10.0, and
 c. has an alkalinity greater than 0.010N to give a catalyst with a weight ratio of nickel to SiO$_2$ between 0.5 and 3.0.
2. A process according to claim 1 in which the weight ratio of nickel to SiO$_2$ is between 2 and 3.
3. An alkaline precipitation process for preparing a supported nickel catalyst according to claim 1 in which
 a. the suspension is formed continuously in a mixing vessel in which the suspension has a mean residence of less than 60 minutes and
 b. the suspension is then filtered, the time between the suspension leaving the mixing vessel and the suspension being filtered being less than 15 minutes.
4. A process according to claim 3 in which the mean residence is between 5 and 15 minutes.

* * * * *

UNITED STATES PATENT OFFICE
CERTIFICATE OF CORRECTION

Patent No. 3,959,181            Dated May 25, 1976

Inventor(s) Hiepke Boerma

It is certified that error appears in the above-identified patent and that said Letters Patent are hereby corrected as shown below:

Claim 1, line 13, delete "3.0" and insert --4.0--.

Signed and Sealed this

Twenty-sixth Day of October 1976

[SEAL]

Attest:

RUTH C. MASON
*Attesting Officer*

C. MARSHALL DANN
*Commissioner of Patents and Trademarks*